United States Patent [19]

Sugano et al.

[11] Patent Number: 5,514,567
[45] Date of Patent: May 7, 1996

[54] DNA AND RECOMBINANT PLASMID

[75] Inventors: Haruo Sugano, Tokyo; Masami Muramatsu, Tokorozawa; Tadatsugu Taniguchi, Tokyo, all of Japan

[73] Assignee: Juridical Foundation, Japanese Foundation For Cancer Research, Tokyo, Japan

[21] Appl. No.: 400,179

[22] Filed: Mar. 6, 1995

Related U.S. Application Data

[60] Continuation of Ser. No. 389,922, Jun. 18, 1982, abandoned, which is a division of Ser. No. 201,359, Oct. 27, 1980, Pat. No. 5,326,859.

[30] Foreign Application Priority Data

Oct. 30, 1979 [JP] Japan .................................. 54-139289
Mar. 19, 1980 [JP] Japan .................................. 55-33931

[51] Int. Cl.⁶ ........................... C12P 21/04; C12N 15/00
[52] U.S. Cl. ................. 435/69.51; 435/91.1; 435/172.3; 435/252.3; 435/252.33; 435/320.1; 536/23.52
[58] Field of Search .............................. 435/69.51, 91.1, 435/243, 252.33, 172.3, 320.1, 252.33; 536/23.52

[56] References Cited

U.S. PATENT DOCUMENTS 4,262,090  4/1981  Colby et al. .............................. 435/91

OTHER PUBLICATIONS

Bethesda Research Laboratories, Inc. 1979 Catalog, pp. 18 and 32.
Fernandez et al, Febs Lett. 87: 277 (1978).
Taniguchi et al., Gene 10, pp. 11–15 (1980).
Houghton, Nature vol. 285, p. 536 (Jun. 19, 1980).
Research Disclosure #18309 (Jul. 1979).
Taniguchi et al., Proc. Japan Acad., 55(B) (Nov. 12, 1979).
Taniguchi et al., Proc. Natl. Acad. Sci., U.S.A., vol. 77(7), 4003 (Jul. 1980).

*Primary Examiner*—James Martinell
*Attorney, Agent, or Firm*—White & Case

[57] ABSTRACT

Disclosed is a recombinant plasmid having a gene which encompasses at least the entire coding region of human fibroblast interferon messenger RNA and a method for preparing such plasmid.

31 Claims, 1 Drawing Sheet

5,514,567

DNA AND RECOMBINANT PLASMID

This application is a continuation of application Ser. No. 06/389,922, now abandoned, filed on Jun. 18, 1982, abandoned, which is a divisional of application Ser. No. 06/201,359 filed Oct. 27, 1980, and issued as U.S. Pat. No. 5,326,859 on Jul. 5, 1994.

BACKGROUND OF THE INVENTION

The present invention relates to a DNA which codes for a polypeptide with interferon activity and a recombinant plasmid containing the DNA. The present invention also pertains to a microorganism containing the recombinant plasmid.

Interferon is a glycoprotein (molecular weight approx. 20,000) with antiviral activity, discovered by Isaacs and Lindenmann in 1957. Subsequent studies have indicated antitumor activity of the substance in addition to antiviral activity and hence a wide clinical application of this substance is expected. For instance, it has been reported that interferon may be effectively administered to various viral diseases, osteosarcoma and mammary carcinoma.

However, because of its high species-specificity, only the interferon derived from human cells can be used for human application. At present, the interferon which is being used for administration has a relative activity of about $10^6$ (International units) per 1 mg, which corresponds to a purity of about 0.1–0.01%.

Moreover, the use of the interferon is quite limited because of difficulties in mass-production. At present even for the interferon requirement for clinical tests ($10^{13}$ units per year), the supply is only about 1%. For these reasons, development of technology to produce human interferon in high purity, with ease and in large quantities is in demand.

To this end, a novel technique has been developed for producing interferon with ease and in a large quantity by inserting a human interferon gene into a plasmid DNA (for instance plasmid DNA derived from *Escherichia coli*) with recombinant DNA (deoxyribonucleic acid) technology.

SUMMARY OF THE INVENTION

In accordance with the present invention, a DNA which codes for a polypeptide with interferon activity is prepared using the human interferon messenger RNA as a template and a novel recombinant plasmid containing the DNA is prepared. In addition, the recombinant plasmid may be inserted into a host microorganism.

The DNA which codes for a polypeptide with interferon activity and the recombinant plasmid containing the DNA have been obtained for the first time by the present inventors. The DNA and the recombinant plasmid may be used, inter alia, for amplification of human interferon in bacteria such as *Escherichia coli*. Such bacteria are then useful for the production of human interferon in large quantities at low cost.

The DNA and the recombinant plasmid of the present invention are prepared by the following general procedure.

First, cytoplasmic RNA is extracted from (1) human fibroblast, MG63 cells or others induced by poly (I): poly (C) which is a double stranded RNA composed of polyinosinic acid and polycytidylic acid or other inducers, (2) human leucocyte, lymphoblastic cells, NAMALWA cells or others induced by Sendai virus or other inducers, or (3) lymphocytes induced by various mitogens or other inducers. From this RNA, the human interferon messenger RNA (hereinafter messenger RNA is referred to as mRNA) containing poly A (polyadenylic acid) is isolated. A double stranded DNA is synthesized, for example, by reverse transcriptase, with the mRNA preparation having high interferon mRNA activity, as a template. A recombinant is obtained by inserting the synthesized DNA into a vector DNA such as *Escherichia coli* plasmid DNA by the technique of in vitro DNA recombination. The recombinant is labelled with a radio isotope for use as a probe. Recombinant plasmids having an inserted portion which is complementary to the human interferon mRNA are selected. The DNA which codes for a polypeptide with interferon activity is recovered from the recombinant plasmid and the base sequence of the DNA is determined.

BRIEF DESCRIPTION OF THE DRAWINGS

FIG. 1 illustrates restriction endonuclease maps of:

(a) a gene which shows complementarity to the human fibroblast interferon mRNA in the recombinant #319 used to make a novel recombinant plasmid #319-13; and (b) a gene which shows complementarity to the human fibroblast interferon mRNA in the novel recombinant plasmid #319-13.

DETAILED DESCRIPTION OF THE PRESENT INVENTION

The present invention relates to a DNA which codes for a polypeptide with interferon activity, a recombinant plasmid containing the DNA and a microorganism containing the recombinant plasmid.

The DNA of the present invention may be a cloned DNA showing complementarity to the human interferon mRNA, a cloned DNA which codes for a polypeptide with interferon activity or a cloned DNA which codes for human interferon polypeptide. Especially a DNA which encompasses the entire coding region of the human fibroblast interferon (i.e. human $\beta_1$ interferon mRNA is a preferred example of the DNA of the present invention.

The recombinant plasmid of the present invention is a recombinant plasmid wherein the DNA mentioned above is inserted in a vector DNA such as pBR322, pCR1 or, pMB9.

The recombinant plasmids named #319 and #319-13 are preferred examples of a recombinant plasmid according to the invention.

The DNA and the recombinant plasmid are inserted in a host microorganism and the transformant can be used to produce a substance having interferon activity.

As the host microorganism, *Escherichia coli* X1776 is preferably used.

An example of the processes of producing the DNA, the recombinant plasmid and the transformant of the present invention is as follows.

First, human fibroblasts may be obtained from fetus-derived foreskin, or the like. A small amount of interferon is then added to a culture fluid of human fibroblasts to prime the interferon synthesis by human fibroblasts, to which poly(I): poly(C) is added to induce the synthesis of interferon mRNA. Cycloheximide is added simultaneously to increase the level of interferon mRNA. At an appropriate time (about 4 hours) after the human fibroblasts are superinduced in the above manner, cells are collected and destroyed and the nuclei are removed. Cytoplasmic total RNA is extracted with phenol, or the like. The RNA can also be extracted by destroying the whole cells, extracting both DNA and RNA with, for example, phenol, and degrading and removing the DNA with DNAase.

Further, interferon mRNA can also be extracted from MG63 cells induced by poly(I): poly(C) or other inducers, human leucocyte or lymphoblastic cells induced by Sendai virus or other inducers, and lymphocytes induced by various mitogens or other inducers.

The thus extracted RNA is dissolved in a salt solution of NaCl or KCl at a high concentration such as 0.5M and put on a column of oligo (dT) cellulose to adsorb mRNA having poly(A) on the column. Elution is carried out with water, a salt solution at a low concentration such as 10 mM Tris-HCl buffer, or the like to isolate mRNA having poly(A).

The isolated mRNA is fractionated by sucrose density gradient centrifugation. Interferon mRNA activity in each fraction is checked by determining interferon activity (antiviral activity) of the protein which is synthesized in oocytes of African claw toad (*Xenopus laevis*) after micro-injecting a part of the mRNA in each fraction. The determination of interferon activity is carried out according to the method described in Japan J. Microbiol. 18, 449–456, (1974).

Then, a DNA showing complementarity to the mRNA is synthesized in vitro by a reverse transcriptase, which is obtained from avian myeloblastosis virus, using, as the template, a mRNA having the highest interferon mRNA activity.

The synthesis is carried out as follows.

A mRNA is reacted at an appropriate temperature (e.g. 37° C.) for an appropriate period (e.g. 60 min.) with oligo (dT), $MgCl_2$ (e.g. 5 mM), NaCl (e.g. 30 mM), mercaptoethanol (e.g. 5 mM) and Tris-HCl buffer (e.g. pH 8.0, 40 mM) using a reverse transcriptase together with deoxyadenosine triphosphate (dATP), deoxythymidine triphosphate (dTTP), deoxyguanosine triphosphate (dGTP) and deoxycytidine triphosphate (dCTP) (e.g. 0.5 mM each) as substrates.

The thus obtained reaction product is subjected to deproteinization with, for example, phenol, and the template RNA is removed by alkali or ribonuclease treatment. A double stranded DNA is synthesized by a reverse transcriptase in a similar way as the synthesis of the DNA showing complementarity to mRNA described above except that mRNA is replaced by DNA and oligo(dT) is omitted.

By using *Escherichia coli* DNA polymerase I which can be obtained from *Escherichia coli* MRE 600, or the like, instead of reverse transcriptase, the same double stranded DNA can be synthesized.

After the double stranded DNA which is synthesized by the above described procedure is treated with Nuclease $S_1$ which can be obtained from *Aspergillus oryzae* in the presence of $ZnCl_2$ (e.g. 1 mM), sodium acetate buffer (e.g. 0.1M, pH 4.5), NaCl (e.g. 0.2M), etc., deoxyadenine chains are formed at both 3' ends of the synthesized DNA by incubating with a terminal transferase purified from calf thymus in the presence of potassium cacodylate buffer (e.g. pH 7.6, 0.14M), Tris (base) (e.g. 0.03M), dithiothreitol (e.g. 0.1 mM), $CoCl_2$ (e.g. 1 mM) and dATP (e.g. 1 mM) at an appropriate temperature (e.g. 37° C.) for an appropriate period (e.g. 20 min.)

On the other hand, a plasmid DNA which is used as a vector DNA, e.g. *Escherichia coli* plasmid pBR322 DNA [Gene vol. 2, p. 95–113 (1977)], is cleaved at one site by treating with a restriction endonuclease EcoRI, which can be obtained, for example, from *Escherichia coli* RY13, in the presence of Tris HCl buffer (e.g. pH 7.5, 10 mM), $MgCl_2$ (e.g. 6 mM), NaCl (e.g. 0.1M), mercaptoethanol (e.g. 6 mM), or the like and then treated with phage λ-derived exonuclease, which can be obtained, for example, from *Escherichia coli* W3102 (λ cI851) x 13), in the presence of Na-glycine buffer (e.g. pH 9.5, 0.1M), $MgCl_2$ (e.g. 5 mM), or the like. Thereafter deoxythymidine chains are formed at both 3' ends in the same way as for the above-described synthesized double stranded DNA by using dTTP instead of dATP.

Synthetic double stranded DNA and plasmid DNA which are chain-elongated at both 3' ends as described above are incubated at an appropriate temperature for an appropriate period with Tris-HCl buffer (e.g. pH 7.5, 50 mM), NaCl (e.g. 0.1M), EDTA (e.g. 5 mM), or the like and hybridized with hydrogen bonds formed by adenine and thymine. Then, a transformable *Escherichia coli* strain, e.g. *Escherichia coli* x1776 (Molecular Cloning of Recombinant DNA, Scott, W. A. & Werner, R. edited, Academic Press p. 99–114, 1977) is transformed with the hybridized DNA by the method of Enen et al. (J. Mol. Biol. vol. 96, p. 495–509, 1975) or the like.

In the novel recombinant plasmid DNA thus obtained, there exists a vector DNA gene, e.g. β-lactamase (enzyme that destroys ampicillin) gene, of *Escherichia coli* plasmid pBR322. Therefore, the transformed *Escherichia coli* shows resistance to ampicillin. The following technique is used to pick up a strain with a novel recombinant having a gene which shows complementarity to the human interferon messenger RNA among these ampicillin resistant strains.

First, [$^{32}$P] labelled DNA is synthesized with the RNA having interferon mRNA activity described above as a template and the DNA is hybridized with mRNA extracted, without induction by poly(I): poly(C) (therefore, interferon mRNA synthesis is not induced), from the human fibroblasts by incubating at a high temperature (e.g. 65° C.) in a reaction mixture containing, for example NaCl (e.g. 0.5M). Then, the hybridized DNA (Probe A) and non-hybridized DNA (Probe B) are separated by hydroxyapatite column chromatography. Next, filter-fixed DNAs of transformants are hybridized separately with Probe B or Probe A according to the technique of Grunstein-Hogness (Proc. Nat. Acad. Sci. USA, vol. 72, p. 3961–3965, 1975) and strains having a DNA hybridizable with Probe B but not or barely with Probe A are discerned by autoradiography.

Then, plasmid DNA is isolated from each of the discriminated strains and hybridized with mRNA having interferon mRNA activity by incubating at a high temperature (e.g. 53° C.) in the presence of 80% (w/v) formamide, 0.4M NaCl, etc. Since the mRNA hybridized with cDNA portion of the plasmid DNA from the above-described strain can be retained on a nitrocellulose filter, whereas unhybridized mRNA can not under certain conditions (refer to Example below and Nygaard, A. P. & Hall, B. D., Biochem. Biophys. Res. Commun. Vol. 12, p. 98–104, 1963) this mRNA can be recovered selectively from the filter at a high temperature (e.g. 60° C.) in a solution such as 90% (v/v) formamide and thereafter injected into oocytes of *Xenopus laevis*.

When interferon is synthesized in the oocytes, the DNA used for hybridization must contain a DNA which is complementary to interferon mRNA; and by this method, a recombinant plasmid DNA having a gene showing complementarity to the human fibroblast interferon mRNA can be isolated.

The recombinant plasmid DNA obtained above or segments cleaved with a restriction endonuclease are labelled with a radio isotope such as $^{32}$P by Nick-translation method (Rigby, et al., J. Mol. Biol. vol. 113, p. 237–251, 1977), or the like, and used as a probe to obtain *Escherichia coli* strains containing a recombinant plasmid having the interferon mRNA sequence from the above ampicillin resistant strains in the same way as described above. Several strains thus obtained are cultured and the plasmid DNA is isolated therefrom. The plasmid DNA is cleaved with a restriction endonuclease to obtain the inserted DNA. The length of the inserted DNA is investigated to obtain a plasmid having an inserted DNA coding the entire region of the interferon protein. Primary structure of the inserted DNA of one of recombinant plasmids isolated by the above method is determined according to the Maxam-Gilbert method (Proc. Nat. Acad. Sci. U.S.A. vol. 74, p. 560–564, 1977) and is illustrated in the following Example. It has thus been shown that the recombinant plasmid of the invention contains the entire coding region of the human fibroblast interferon mRNA.

As outlined above, a DNA which codes for human fibroblast interferon polypeptide, especially a DNA which encompasses the entire coding region of the human fibroblast interferon mRNA, a recombinant plasmid containing the DNA and a microorganism containing the plasmid are prepared.

The base sequence of the DNA obtained above and the corresponding peptide sequence are illustrated in Table 5 below.

The base sequence in Table 5 is a preferred example for the expression of the DNA which codes for human interferon polypeptide. Since the amino acids in the peptide sequence in Table 5 may be coded for by a base triplet other than those in Table 5, base sequences of the DNA which codes for human interferon polypeptide other than that in Table 5 are also included in the present invention.

The determination of the base sequence of the DNA which codes for human interferon polypeptide according to the present invention has enabled the chemical synthesis of such DNA.

The present novel recombinant plasmids having a gene which encompasses at least the entire coding region of the human fibroblast interferon mRNA are very useful because they enable mass production of interferon in *Escherichia coli* or in eukaryctic cells which can be grown on a large scale.

Recombinant plasmids containing a DNA using, as a template, leucocyte mRNA or immune interferon mRNA can be prepared by the same method as mentioned above and such plasmids are also expected to be useful for the mass production of interferon.

One specific embodiment of the present invention is illustrated by the following representative example.

EXAMPLE

After priming of human fibroblasts by overnight incubation with MEM culture medium (product of Nissui Seiyaku Co., Ltd., Japan) containing human interferon which is prepared according to the method described in Proc. Nat. Acad. Sci. USA, 73, 520–523 (1976) (25 U/ml), the fibroblasts were superinduced by adding 10 µg/ml of poly(I): poly(C) (product of Galbiochem Co., USA) and 5 µg/ml of cycloheximide to the medium. The priming and superinduction are carried out according to the methods described in Brit. J. Exp. Path., 39, 452–458 (1958) and Antimicrob. Agents Chemother., 2, 476–484 (1972), respectively.

After 4 hours, $1.5 \times 10^9$ superinduced human fibroblasts were destroyed by Teflon homogenizer (sold by Takashima Shoten Co., Japan) at a temperature of 0° to 4° C. in the presence of 0.3% NP-40 (product of Daiichi Kagaku Co., Japan) and 50 µg/ml heparin in RSB buffer (10 mM Tris-HCl, pH 7.5; 10 mM NaCl; 1.5 mM $MgCl_2$). Nuclei were removed by centrifugation at 3000 rpm and 4° C. for 10 minutes and 9.6 mg of cytoplasmic RNA was obtained by extraction 3 times with phenol.

The cytoplasmic RNA was precipitated with 67% ethanol in the presence of 0.1M NaCl, dissolved in 10 ml of 1 mM EDTA solution and incubated at 65° C. for 2 minutes. Then, 2.5 ml of a salt solution at a high concentration (0.5M Tris-HCl, pH 7.5; 1M NaCl; 50 mM EDTA) was added to the above solution and the mixture was put on a column packed with 0.15 g of an oligo (dT) cellulose (product of P-L Biochemicals Co., USA) to adsorb mRNA containing poly(A). Elution was then carried out with a salt solution at a low concentration (10 mM Tris-HCl, pH 7.5) and water to isolate 250 µg of mRNA containing poly(A).

The mRNA was precipitated with 67% ethanol in the presence of 0.1M NaCl and dissolved in 0.5 ml of 1 mM EDTA solution. The solution was incubated at 65° C. for 2 minutes, subjected to centrifugation through a 5–25% sucross-density gradient containing 50 mM Tris-HCl, pH 7.5, 0.2M NaCl and 1 mM EDTA (rotated at 35,000 rpm using the SW40 rotor of Beckmann Co., U.S.A.) at 4° C. for 16 hrs. and fractionated into 20 fractions.

The interferon mRNA activity of each of these fractions was determined as mentioned above, and the results are shown in Table 1 below.

TABLE 1

| Fraction No. | Interferon Activity |
| --- | --- |
| 9 | <50 units/ml |
| 10 | 44 |
| 11 | 550 |
| 12 | 52 |

The mRNA in Fraction No. 11 was approximately 5 µg. This mRNA and a reverse transcriptase were incubated at 37° C. for an hour in 20 µl of a reaction mixture consisting of 5 µg mRNA; 0.5 mM dATP; 0.5 mM dTTP; 0.5 mM dGTP; 0.5 mM dCTP; 1 µg oligo(dT) (product of P-L Biochemicals Co., USA); 8 units reverse transcriptase (derived from Avian myeloblastisis virus, for example, product of Life Science Inc. Florida, USA); 5 mM $MgCL_2$; 30 mM NaCl; 5 mM mercaptoethanol; and 40 mM Tris-HCl (pH 8.0) and then deproteinized with phenol. After RNA was removed by treatment with 0.3N NaOH at 37° C. for 15 hours, the synthesized single stranded DNA was incubated at 37° C. in 20 µl of a reaction mixture [the same mixture as described above except that mRNA and oligo (dT) were omitted] for one hour to synthesize 1.5 µg of a double stranded DNA.

The double stranded DNA was treated with Nuclease $S_1$ (product of Bethesda Research Laboratories Inc., USA which is referred to as BRL, hereinafter) in 50 µl of a reaction mixture (1.5 µg double stranded DNA: 1 mM $AnCl_2$; 0.1M sodium acetate, pH 4.5; 0.2M NaCl; 0.05 unit $S_1$) at 37° C. for 30 minutes and the enzyme was removed by phenol extraction. The DNA was precipitated with ethanol and then treated with a terminal transferase in 20 µl of a reaction mixture consisting of 1.5 µg DNA; 0.14M potassium cacodylate, pH 7.6; 0.03M Tris (base); 0.1 mM dithiothreitol; 1 mM $CoCl_2$; 1 mM dATP; and 1 unit terminal transferase (product of BRL) at 37° C. for 20 minutes to obtain about 1.5 μg of a product wherein 100 deoxyadenosine chains were formed at both 3' ends of the double-stranded DNA.

On the other hand, 10 μg of *Escherichia coli* plasmid pBR322 DNA (product of BRL) was treated at 37° C. for 2 hours with a restriction endonuclease EcoRI in 100 μl of a reaction mixture consisting of 10 mM Tris-HCl, pH 7.5; 6 mM MgCl$_2$; 0.1M NaCl; 6 mM mercaptoethanol; and 10 units EcoRI (product of BRL) leading to the cleavage at the only one cutting site in pBR322 DNA. The cut plasmid DNA was treated with an exonuclease derived from phage λ in 200 μl of a reaction mixture consisting of 10 μg DNA; 0.1M Naglycine, pH 9.5; 5 mM MgCl$_2$; 50 μg/ml albumin (product of Miles Laboratories Inc., USA) at 0° C. for 90 minutes and the enzyme was removed by phenol extraction. The DNA was treated with a terminal transferase in 50 μl of a reaction mixture [10 μg DNA; 0.14M potassium cacodylate, pH 7.6; 0.03M Tris (base); 0.1 mM dithiothreitol; 1 mM CoCl$_2$; 1 mM dTTP; 2 units terminal transferase] at 37° C. for 20 minutes to obtain about 0.5 μg of a product wherein 100 deoxythymidine chains were formed at both 3' ends of plasmid pBR322 DNA described above.

Then, 0.02 μg of the synthesized double stranded DNA obtained above, and 0.1 μg of the plasmid pBR322 DNA were incubated for hybridization in a solution containing 0.1M NaCl, 50 mM Tris-HCl (pH 7.5) and 5 mM EDTA at 65° C. for 2 minutes, at 45° C. for one hour, at 37° C. for one hour and at room temperature for one hour. Then, *Escherichia coli* X1776 was transformed with the hybridized recombinant following the method of Enea et al.

About 4,000 ampicillin-resistant strains were isolated by this method. 3,600 resistant strains were chosen, and the DNA of each strain was fixed on nitrocellulose filters in duplicate (Grunstein-Hogness Method).

On the other hand, [$^{32}$P] labelled single stranded DNA was synthesized (about 0.44 μg, specific radioactivity approx. 6×10$^8$ c.p.m./μg) by a reverse transcriptase in the same way as that for single stranded DNA mentioned above (dCTP was labelled with $^{32}$P) using the interferon mRNA fraction (about 10 μg) which had been extracted and partially purified as described above, as a template. The DNA was hybridized in 50 μl of a reaction mixture (25 μg mRNA; 0.45 μg single stranded DNA labelled with $^{32}$P; 0.5M NaCl; 25 mM Pipes buffer, pH 6.5) at 65° C. for 40 hours with 25 μg of mRNA extracted from human fibroblasts which had not been induced by poly (I): poly (C). The latter mRNA was prepared by the same method used to extract poly (I): poly (C)-induced mRNA. The reaction mixture was put on a column packed with 0.2 g of a hydroxyapatite, and elution was first carried out with 5 ml of 0.14M phosphate buffer (pH 6.5) to elute the single stranded DNA, and then with 5 ml of 0.4M phosphate buffer to elute the DNA hybridized with RNA. As the result, the DNA (about 90% of the whole) (Probe A) which hybridized with the mRNA mentioned above, and the DNA (about 10% of the whole) (Probe B) which did not hybridize were isolated.

Each probe was then hybridized separately with the above DNA fixed on the nitrocellulose filters according to the Grunstein-Hogness method. Four strains were identified which reacted mainly to Probe B but little to Probe A by autoradiography.

Table 2 shows the extent of reaction of the DNAs from the four strains to each probe as revealed by autoradiogram.

TABLE 2

| Ampicillin-resistant strains | Extent of Reaction of Probe with DNA in the strains | |
|---|---|---|
| | Probe A | Probe B |
| #319 | ++ | ++++ |
| #644 | + | +++ |
| #746 | − | ++ |
| #3578 | + | +++++ |

Plasmid DNA was isolated from cells of the four strains by the method of Currier and Nester (Analyt. Biochem. vol. 76, p. 431–441, 1976). Then, these DNAs were hybridized with the interferon mRNA as follows.

First, 5 μg of plasmid DNA was linearized by incubating with restriction endonuclease Hind III which can be obtained from Haemophilus influenzae Rd in 50 μl of a reaction mixture consisting of 10 mM Tris-HCl, pH 7.5; 6 mM MgCl$_2$; 50 mM NaCl; 6 mM mercaptoethanol; and 5 units Hind III (product of BRL) at 37° C. for 2 hours. After deproteinization by phenol extraction, the DNA was precipitated with ethanol and dissolved in 20 μl of 80% (w/v) formamide. The solution was denatured at 85° C. for 10 minutes and was then incubated in a solution consisting of 2.5 μg mRNA, 20 μl 80% (w/v) formamide, 20 mM Pipes buffer (pH 6.5), 0.4M NaCl and 5 mM EDTA, at 53° C. Four hours later the mixture was mixed with 0.4 ml of 3×SSC (1×SSC corresponds to 0.15M NaCl, 0.015M sodium citrate) at 0° C., and was filtered through a nitrocellulose filter (diameter: 1 cm, pore size: 0.45 μm) at a rate of about 0.5 ml per minute. After washing the filter with about 1.5 ml of 2×SSC, the filter was immersed in a solution consisting of 0.6 ml of 90% (v/v) formamide, 20 mM Pipes buffer, 0.1% SDS (sodium dodecylsulfate) and 5 mM EDTA. Incubation of the filter at 60° C. for 2 minutes and the removal of the solution were repeated 3 times and the RNA eluted from the nitrocellulose filter into the solution (1.8 ml) was precipitated with ethanol in the presence of 0.1M NaCl. The mRNA containing poly(A) was isolated from the RNA by using oligo (dT) cellulose column chromatography, dissolved in a mixture of 3 μl of 10 mM Tris-HCl (pH 7.5) and 88 mM NaCl and injected into the oocytes of *Xenopus laevis*. After 15 hours, the interferon synthesized in the oocytes was determined (antiviral activity).

Table 3 shows the interferon mRNA activity of the mRNA which has hybridized with the DNA derived from the four bacterial strains mentioned above.

TABLE 3

| Bacterial strain | Interferon mRNA activity (unit/ml) |
|---|---|
| #319 | 360 |
| #644 | <10 |
| #746 | 15 |
| #3578 | <10 |
| pBR322DNA | <10 |

Five μg of plasmid DNA obtained from strain #319 by the Currier and Nester method was cleaved with restriction endonuclease Hind III in the same manner as mentioned above. The DNA and the recombinant plasmid βGpBR322 DNA (the vector was pBR322) (obtained from the Institute for Molecular Biology I of University of Zurich or prepared by the method described in Nature 281, 40–46, 1979) containing rabbit β-globin gene, separately or as a mixture, were hybridized with a mixture of rabbit globin mRNA (obtained from rabbit red blood cells) (1 μg) and interferon mRNA (2.5 μg) obtained from human fibroblasts under the same conditions as mentioned above. The mRNA which formed a hybrid was injected into the oocytes of *Xenopus laevis*. The oocytes were then incubated for 15 hours in Barth's culture medium (J. Embryol. Exp. Morph. 7, 210, 1959) containing [$^3$H] labelled histidine and [$^3$H] labelled globin was isolated by acrylamide gel electrophoresis and determined quantitatively by fluorography according to the method described in Eur. J. Biochem. 46, 83–88, (1974). The interferon was determined by antiviral activity as described above. The synthesis of rabbit β-globin and the human interferon was determined in this way. The result is shown in Table 4 below.

TABLE 4

| DNA | Synthesized interferon activity | Amount of globin synthesized |
|---|---|---|
| #319 | 200 (units/ml) | – |
| βGpBR322 | 35 | ++++ |
| mixture of both plasmids | 160 | +++ |

From the result of this experiment it has been established that DNA of #319 has DNA (the interferon gene) which forms a hybrid specifically with the interferon mRNA.

Figure 1:
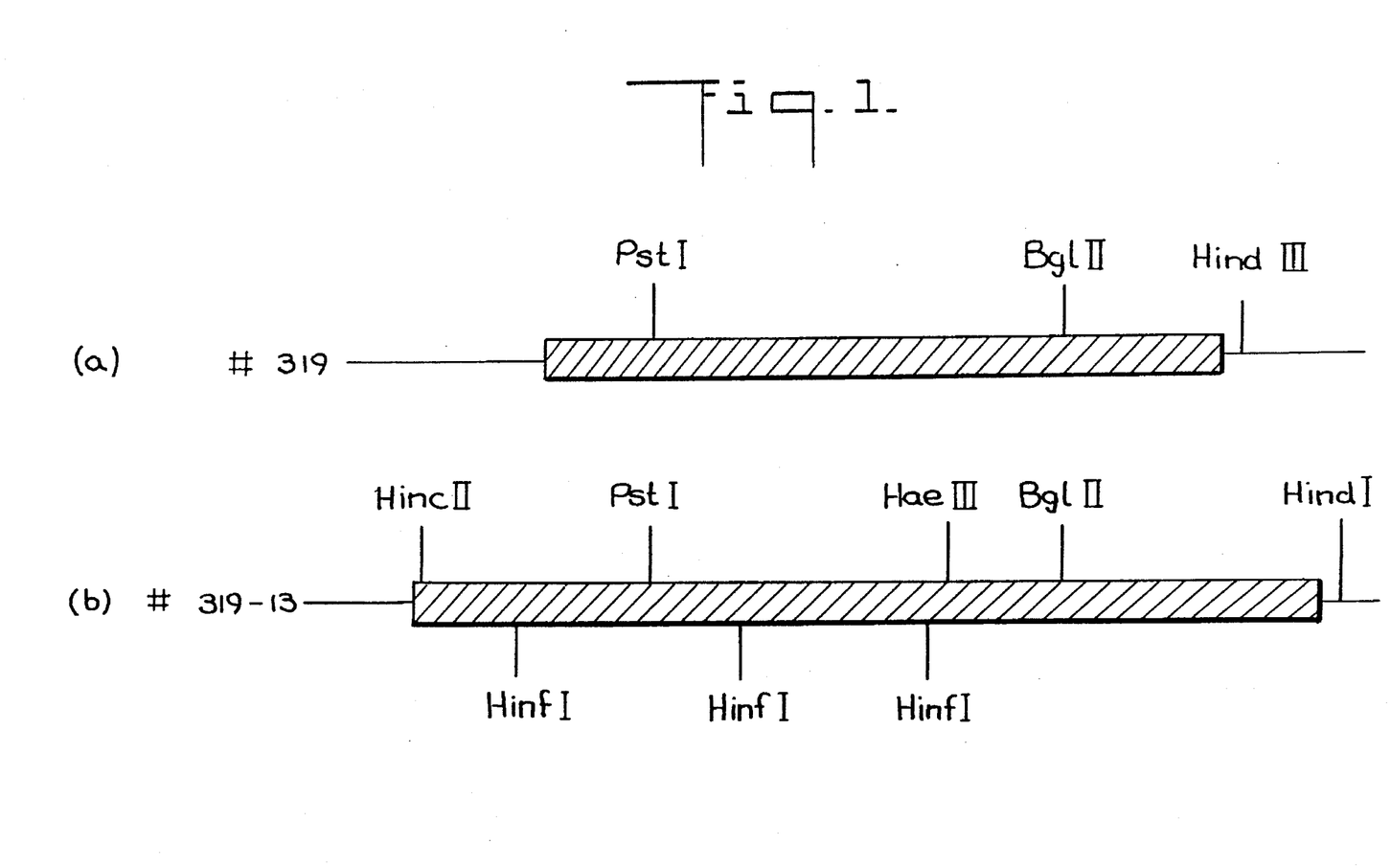

The DNA of #319 was cleaved with several restriction endonucleases and a restriction endonuclease map, FIG. 1(a), was made by agalose electrophoresis.

Restriction endonucleases, Pst I, Bgl II and Hind III (sold by BRL, etc.) cleave #319 DNA at the sites illustrated in FIG. 1(a).

The segments obtained by cleaving #319 DNA with restriction endonucleases Pst I and Bgl II were isolated and purified by gel electrophoresis according to the method of Tabak & Flavell (Nucleic Acids Research, vol. 5, p. 2321–2332, 1978). The segments were labelled with $^{32}$P according to the method of Rigby, et al. (J. Mol. Biol. vol. 113, p. 237–251, 1977) and the labelled segment was used as a probe. Several strains containing a plasmid which shows complementarity to the probe were isolated from the above ampicillin-resistant strains according to the above method of Grunstein & Hogness (Proc. Nat. Acad. Sci. U.S.A., vol. 72, p. 3961–3965, 1975), namely, colony hybridization method. Plasmid DNAs were obtained from each of the strains according to the above method of Currier-Nester and the inserted portions thereof were cleaved with a restriction endonuclease such as Hind III. The cut plasmid DNA segments were compared in length and the longest plasmid DNA segment was selected. The plasmid was named #319-13.

The restriction endonuclease map of the plasmid is illustrated in FIG. 1 (b) which substantiates that the novel plasmid has an mRNA sequence containing the mRNA sequence of #319. Primary structure (base sequence) of the mRNA sequence inserted in the plasmid of #319-13 was determined by the method of Maxam-Gilbert (Proc. Nat. Acad. Sci, U.S.A. vol. 74, p. 560–564, 1977). The primary structure is given in Table 5 below.

TABLE 5

```
              -20                                         -10                                              1
          MET THR ASN LYS CYS LEU LEU GLN ILE ALA LEU LEU SER THR THR ALA LEU SER TYR
          ATG ACC AAC AAG TGT CTC CTG CAA ATT GCT CTC CTG TCC ACT ACA GCT CTT TCC TAC ATG
GTC AAC   TAC TGG TTG TTC ACA GAG GAC GTT TAA CGA GAG GAC AGG TGA TGT CGA GAA AGG ATG TAC
CAG TTG
                      20                                40                                 60

ASN LEU GLY PHE PHE  GLN ARG SER ASN PHE         GLN LEU ASN GLY ARG LEU GLU
AAC CTT GGA TTC CTA  CAA AGA AGC AAT TTT     GCT CAG CTG TGG AAG CTT GAA
TTG GAA CCT AAG GAT  GTT TCT TCG TTA AAA     CGA GTC GAC ACC TTC GAA CTT
            20                              10                          60

TYR CYS LYS ASP ARG MET PHE ASN PHE          GLU ILE LYS GLN LEU PHE GLN LYS GLU ASP ALA
TAT TGC AAG GAC AGG ATG TTT AAC TTT     CCT GAG ATT AAG CAG CTG TTC CAG AAG GAG GAC GCC
ATA ACG TTC CTG TCC TAC AAA TTG AAA     GGA CTC TAA TTC GTC GAC AAG GTC TTC CTC CTG CGG
        160                             100               40                      220   140
                      180                                  200             70           80
                                                    40          50                              ASN GLU
ALA LEU THR ILE VAL TYR ILE GLU ASP TYR LEU     MET LEU ASN GLN PHE ALA ILE PHE LYS HIS ASP LEU LYS GLY SER SER GLY
GCA TTG ACC ATC GTT TAT ATA GAG GAC TAT CTA     ATG CTG AAC CAG ATC GCT TTT AAA CAT GAT CTA CTG AAA GGC AGC TCA AGT
CGT AAC TGG TAG CAA ATA TAG CTC CTG ATA GAT     TAC GAC TTG GTC TAG CGA AAA TTT GTA CTA GAT GAC TTT CCG TCG AGT TCA
        240                                             260                          300
                                                                                          100
THR ILE VAL GLU ASN LEU LEU ALA LEU VAL TYR HIS GLN ILE ASN ILE THR SER TRP ILE LEU ARG TYR TYR GLY ARG VAL LEU GLU
ACT ATT GTT GAG AAC CTG CTG GCT CTG GTC TAT CAT CAG ATA AAC ATA ACA AGT TGG ATC CTA AGG TAT TAT GGG AGG GTC CTG GAG
TGA TAA CAA CTC TTG GAC GAC CGA GAC CAG ATA GTA GTC TAT TTG TAT TGT TCA ACC TAG GAT TCC ATA ATA CCC TCC CAG GAC CTC
            320                             340                                    360                  380

120
LYS GLU PHE ASP ARG GLY LYS LEU MET SER SER ALA TRP THR PHE ARG LEU     LEU HIS LEU GLN ASN HIS LEU LYS LEU GLU
AAA GAA TTC GAT AGG GGA AAA CTC ATG AGC AGT GCC TGG ACC TTC AGG CTT     CTG CAC CTG CAA AAC CAT GTA GAC CTG GAA
TTT CTT AAG CTA TCC CCT TTT GAG TAC TCG TCA CGG ACC TGG AAG TCC GAA     GAC GTG GAC GTT TTG GTA CAT CTG GAC CTT
            400                                    420                          440                         460
                                                                                       130
LYS ALA LYS LYS TYR SER HIS CYS ALA THR PHE LEU ASP     VAL ARG GLU LEU ARG VAL GLU ILE LEU GLY ARG LEU GLU LEU HIS TYR PHE ILE ASN ARG
AAG GCC AAG AAG TAC AGT CAC TGT GCC ATA ACC TTT CTA     GTG AGA GAA CTA AGA GTC GAA ATC CTA GGG AGG TTT CAT TAC TTC ATT AAC AGA
TTC CGG TTC TTC ATG TCA GTG ACA CGG TGG AAA GAT         CAC TCT CTT GAT TCT CAG CTT TAG GAT CCC TCC AAA GTA ATG AAG TAA TTG TCT
            480                                                     520                                540
                          140                                       150
```

TABLE 5-continued

```
160                     166
LEU THR GLY TYR LEU ARG ASN
CTT ACA GGT TAC CTC CGA AAC TGA AGA TCT CCT AGC CTG TGC CTC TGG GAC TGG ACA ATT GCT TCA AGC ATT CTT CAA
GAA TGT CCA ATG GAG GCT TTG ACT TCT AGA GGA TCG GAC ACG GAG ACC CTG ACC TGT TAA CGA AGT TCG TAA GAA GTT
                        560                 580                 600                 620

CCA GCA GAT GCT GTT TAA GTG ACT GAT GGC TAA TGT ACT GCA TAT GAA AGG ACA GAA GAT TTT GAA AT TTTT ATT
GGT CGT CTA CGA CAA ATT CAC TGA CTA CCG ATT ACA TGA CGT ATA CTT TCC AGT GAT CTT CTA AAA CTT TAA AAA TAA
                        640                 660                 680                 700

AAA TTA TGA GTT ATT TTT ATT TAT TTA AAT TTT ATT TTG GAA AAT AAA TTA TTT AAT AAA CTT TTG GTG CAA AAG TCA AAA AAA
TTT AAT ACT CAA TAA AAA TAA ATA AAT TTA AAA TAA AAC CTT TTA TTT AAT AAA TTA TTT GAA AAC CAC GTT TTC AGT TTT TTT
                        720                 740                 760
```

The DNA sequence permits prediction of the entire amino acid sequence for human fibroblast interferon (amino acids 1-166) and its putative signal peptide (amino acids −21 to −1) as shown in the line above the DNA sequences.

It is important that in the sequence there exist without any errors the base sequence (three base pairs) corresponding to the amino acid sequence from the amino-terminal to 13th amino acid of the human fibroblast interferon reported by Knight, et al. (Science vol. 207, p. 525–526, 1980). This fact establishes that the #319-13 plasmid of the present invention has the human fibroblast interferon mRNA sequence.

Further, it is apparent from the data of the primary sequence that the plasmid encompasses the entire coding region of the protein of the above mRNA and probably the coding region of the signal peptide.

Therefore, transformation of the plasmid or mRNA inserted therein to other expression plasmids enables a host such as *Escherichia coli* to produce interferon. For such purposes, the #319-13 plasmid which is named TpIF 319-13, transformed in *Escherichia coli* X1776, has been deposited with the American Type Culture Collection, Rockville, Md., U.S.A. under accession number ATCC 31712 and is freely available to the public.

What is claimed is:

1. A recombinant plasmid wherein a DNA which codes for the amino acid sequence:

| | | | | | | | | | |
|---|---|---|---|---|---|---|---|---|---|
| Met | Thr | Asn | Lys | Cys | Leu | Leu | Gln | Ile | Ala |
| | | | | Leu | Leu | Leu | Cys | Phe | Ser |
| Thr | Thr | Ala | Leu | Ser | Met | Ser | Tyr | Asn | Leu |
| | | | | Leu | Gly | Phe | Leu | Gln | Arg |
| Ser | Ser | Asn | Phe | Gln | Cys | Gln | Lys | Leu | Leu |
| | | | | Trp | Gln | Leu | Asn | Gly | Arg |
| Leu | Glu | Tyr | Cys | Leu | Lys | Asp | Arg | Met | Asn |
| | | | | Phe | Asp | Ile | Pro | Glu | Glu |
| Ile | Lys | Gln | Leu | Gln | Gln | Phe | Gln | Lys | Glu |
| | | | | Asp | Ala | Ala | Leu | Thr | Ile |
| Tyr | Glu | Met | Leu | Gln | Asn | Ile | Phe | Ala | Ile |
| | | | | Phe | Arg | Gln | Asp | Ser | Ser |
| Ser | Thr | Gly | Trp | Asn | Glu | Thr | Ile | Val | Glu |
| | | | | Asn | Leu | Leu | Ala | Asn | Val |
| Tyr | His | Gln | Ile | Asn | His | Leu | Lys | Thr | Val |
| | | | | Leu | Glu | Glu | Lys | Leu | Glu |
| Lys | Glu | Asp | Phe | Thr | Arg | Gly | Lys | Leu | Met |
| | | | | Ser | Ser | Leu | His | Leu | Lys |
| Arg | Tyr | Tyr | Gly | Arg | Ile | Leu | His | Tyr | Leu |
| | | | | Lys | Ala | Lys | Glu | Tyr | Ser |
| His | Cys | Ala | Trp | Thr | Ile | Val | Arg | Val | Glu |
| | | | | Ile | Leu | Arg | Asn | Phe | Tyr |
| Phe | Ile | Asn | Arg | Leu | Thr | Gly | Tyr | Leu | Arg |
| | | | | | | | | | Asn | is inserted in a vector DNA.

2. A microorganism containing the recombinant plasmid defined in claim 1.

3. The microorganism according to claim 2 which is *Escherichia coli* X1776.

4. The recombinant plasmid according to claim 1 wherein said inserted DNA comprises the following base pair sequence:

| | | | | | | | | | | | | | | |
|---|---|---|---|---|---|---|---|---|---|---|---|---|---|---|
| ATG | ACC | AAC | AAG | TGT | CTC | CTC | CAA | ATT | GCT | CTC | CTG | TTG | TGC | TTC | TCC |
| TAC | TGG | TTG | TTC | ACA | GAG | GAG | GTT | TAA | CGA | GAG | GAC | AAC | ACG | AAG | AGG |
| ACT | ACA | GCT | CTT | TCC | ATG | AGC | TAC | AAC | TTG | CTT | GGA | TTC | CTA | CAA | AGA |
| TGA | TGT | CGA | GAA | AGG | TAC | TCG | ATG | TTG | AAC | GAA | CCT | AAG | GAT | GTT | TCT |
| AGC | AGC | AAT | TTT | CAG | TGT | CAG | AAG | CTC | CTG | TGG | CAA | TTG | AAT | GGG | AGG |
| TCG | TCG | TTA | AAA | GTC | ACA | GTC | TTC | GAG | GAC | ACC | GTT | AAC | TTA | CCC | TCC |
| CTT | GAA | TAT | TGC | CTC | AAG | GAC | AGG | ATG | AAC | TTT | GAC | ATC | CCT | GAG | GAG |
| GAA | CTT | ATA | ACG | GAG | TTC | CTG | TCC | TAC | TTG | AAA | CTG | TAG | GGA | CTC | CTC |
| ATT | AAG | CAG | CTG | CAG | CAG | TTC | CAG | AAG | GAG | GAC | GCC | GCA | TTG | ACC | ATC |
| TAA | TTC | GTC | GAC | GTC | GTC | AAG | GTC | TTC | CTC | CTG | CGG | CGT | AAC | TGG | TAG |
| TAT | GAG | ATG | CTC | CAG | AAC | ATC | TTT | GCT | ATT | TTC | AGA | CAA | GAT | TCA | TCT |
| ATA | CTC | TAC | GAG | GTC | TTG | TAG | AAA | CGA | TAA | AAG | TCT | GTT | CTA | AGT | AGA |
| AGC | ACT | GGC | TGG | AAT | GAG | ACT | ATT | GTT | GAG | AAC | CTC | CTG | GCT | AAT | GTC |
| TCG | TGA | CCG | ACC | TTA | CTC | TGA | TAA | CAA | CTC | TTG | GAG | GAC | CGA | TTA | CAG |
| TAT | CAT | CAG | ATA | AAC | CAT | CTG | AAG | ACA | GTC | CTG | GAA | GAA | AAA | CTG | GAG |
| ATA | GTA | GTC | TAT | TTG | GTA | GAC | TTC | TGT | CAG | GAC | CTT | CTT | TTT | GAC | CTC |
| AAA | GAA | GAT | TTC | ACC | AGG | GGA | AAA | CTC | ATG | AGC | AGT | CTG | CAC | CTG | AAA |
| TTT | CTT | CTA | AAG | TGG | TCC | CCT | TTT | GAG | TAC | TCG | TCA | GAC | GTG | GAC | TTT |
| AGA | TAT | TAT | GGG | AGG | ATT | CTG | CAT | TAC | CTG | AAG | GCC | AAG | GAG | TAC | AGT |
| TCT | ATA | ATA | CCC | TCC | TAA | GAC | GTA | ATG | GAC | TTC | CGG | TTC | CTC | ATG | TCA |
| CAC | TGT | GCC | TGG | ACC | ATA | GTC | AGA | GTG | GAA | ATC | CTA | AGG | AAC | TTT | TAC |
| GTG | ACA | CGG | ACC | TGG | TAT | CAG | TCT | CAC | CTT | TAG | GAT | TCC | TTG | AAA | ATG |
| TTC | ATT | AAC | AGA | CTT | ACA | GGT | TAC | CTC | CGA | AAC | | | | | |
| AAG | TAA | TTG | TCT | GAA | TGT | CCA | ATG | GAG | GCT | TTG. | | | | | |

5. The recombinant plasmid according to claim 1 wherein said vector DNA is an *Escherichia coli* plasmid.

6. The recombinant plasmid according to claim 5 wherein said *Escherichia coli* plasmid is selected from the group consisting of pBR 322, pCR1 and pMB9.

7. The recombinant plasmid TpIF 319-13.

8. *Escherichia coli* X1776/TpIF 319-13 ATCC 31712.

9. A recombinant plasmid wherein a DNA which codes for the amino acid sequence:

| Met | Ser | Tyr | Asn | Leu | Leu | Gly | Phe | Leu | Gln | Arg | Ser | Ser | Asn | Phe | Gln |
|-----|-----|-----|-----|-----|-----|-----|-----|-----|-----|-----|-----|-----|-----|-----|-----|
| Cys | Gln | Lys | Leu | Leu | Trp | Gln | Leu | Asn | Gly | Arg | Leu | Glu | Tyr | Cys | Leu |
| Lys | Asp | Arg | Met | Asn | Phe | Asp | Ile | Pro | Glu | Glu | Ile | Lys | Gln | Leu | Gln |
| Gln | Phe | Gln | Lys | Glu | Asp | Ala | Ala | Leu | Thr | Ile | Tyr | Glu | Met | Leu | Gln |
| Asn | Ile | Phe | Ala | Ile | Phe | Arg | Gln | Asp | Ser | Ser | Ser | Thr | Gly | Trp | Asn |
| Glu | Thr | Ile | Val | Glu | Asn | Leu | Leu | Ala | Asn | Val | Tyr | His | Gln | Ile | Asn |
| His | Leu | Lys | Thr | Val | Leu | Glu | Glu | Lys | Leu | Glu | Lys | Glu | Asp | Phe | Thr |
| Arg | Gly | Lys | Leu | Met | Ser | Ser | Leu | His | Leu | Lys | Arg | Tyr | Tyr | Gly | Arg |
| Ile | Leu | His | Tyr | Leu | Lys | Ala | Lys | Glu | Tyr | Ser | His | Cys | Ala | Trp | Thr |
| Ile | Val | Arg | Val | Glu | Ilu | Leu | Arg | Asn | Phe | Tyr | Phe | Ile | Asn | Arg | Leu |
| Thr | Gly | Tyr | Leu | Arg | Asn | | | | | | | | | | | is inserted in a vector DNA.

10. A microorganism containing the recombinant plasmid defined in claim 9.

11. The microorganism according to claim 10 which is *Escherichia coli* X1776.

12. The recombinant plasmid according to claim 9 wherein said inserted DNA comprises the following base pair sequence:

| ATG | AGC | TAC | AAC | TTG | CTT | GGA | TTC | CTA | CAA | AGA | AGC | AGC | AAT | TTT | CAG |
|-----|-----|-----|-----|-----|-----|-----|-----|-----|-----|-----|-----|-----|-----|-----|-----|
| TAC | TCG | ATG | TTG | AAC | GAA | CCT | AAG | GAT | GTT | TCT | TCG | TCG | TTA | AAA | GTC |
| TGT | CAG | AAG | CTC | CTG | TGG | CAA | TTG | AAT | GGG | AGG | CTT | GAA | TAT | TGC | CTC |
| ACA | GTC | TTC | GAG | GAC | ACC | GTT | AAC | TTA | CCC | TCC | GAA | CTT | ATA | ACG | GAG |
| AAG | GAC | AGG | ATG | AAC | TTT | GAC | ATC | CCT | GAG | GAG | ATT | AAG | CAG | CTG | CAG |
| TTC | CTG | TCC | TAC | TTG | AAA | CTG | TAG | GGA | CTC | CTC | TAA | TTC | GTC | GAC | GTC |
| CAG | TTC | CAG | AAG | GAG | GAC | GCC | GCA | TTG | ACC | ATC | TAT | GAG | ATG | CTC | CAG |
| GTC | AAG | GTC | TTC | CTC | CTG | CGG | CGT | AAC | TGG | TAG | ATA | CTC | TAC | GAG | GTC |
| AAC | ATC | TTT | GCT | ATT | TTC | AGA | CAA | GAT | TCA | TCT | AGC | ACT | GGC | TGG | AAT |
| TTG | TAG | AAA | CGA | TAA | AAG | TCT | GTT | CTA | AGT | AGA | TCG | TGA | CCG | ACC | TTA |
| GAG | ACT | ATT | GTT | GAG | AAC | CTC | CTG | GCT | AAT | GTC | TAT | CAT | CAG | ATA | AAC |
| CTC | TGA | TAA | CAA | CTC | TTG | GAG | GAC | CGA | TTA | CAG | ATA | GTA | GTC | TAT | TTG |
| CAT | CTG | AAG | ACA | GTC | CTG | GAA | GAA | AAA | CTG | GAG | AAA | GAA | GAT | TTC | ACC |
| GTA | GAC | TTC | TGT | CAG | GAC | CTT | CTT | TTT | GAC | CTC | TTT | CTT | CTA | AAG | TGG |
| AGG | GGA | AAA | CTC | ATG | AGC | AGT | CTG | CAC | CTG | AAA | AGA | TAT | TAT | GGG | AGG |
| TCC | CCT | TTT | GAG | TAC | TCG | TCA | GAC | GTG | GAC | TTT | TCT | ATA | ATA | CCC | TCC |
| ATT | CTG | CAT | TAC | CTG | AAG | GCC | AAG | GAG | TAC | AGT | CAC | TGT | GCC | TGG | ACC |
| TAA | GAC | GTA | ATG | GAC | TTC | CGG | TTC | CTC | ATG | TCA | GTG | ACA | CGG | ACC | TGG |
| ATA | GTC | AGA | GTG | GAA | ATC | CTA | AGG | AAC | TTT | TAC | TTC | ATT | AAC | AGA | CTT |
| TAT | CAG | TCT | CAC | CTT | TAG | GAT | TCC | TTG | AAA | ATG | AAG | TAA | TTG | TCT | GAA |
| ACA | GGT | TAC | CTC | CGA | AAC | | | | | | | | | | |
| TGT | CCA | ATG | GAG | GCT | TTG | | | | | | | | | | |

13. The recombinant plasmid according to claim 9 wherein said vector DNA is an *Escherichia coli* plasmid.

14. The recombinant plasmid according to claim 3 wherein said *Escherichia coli* plasmid is selected from the group consisting of pBR322, pCR1 and pMB9.

15. A process for preparing a recombinant plasmid which comprises inserting a synthesized double stranded DNA which codes for the amino acid sequence:

| Met | Thr | Asn | Lys | Cys | Leu | Leu | Gln | Ile | Ala |
|-----|-----|-----|-----|-----|-----|-----|-----|-----|-----|
| | | | | Leu | Leu | Leu | Cys | Phe | Ser |
| Thr | Thr | Ala | Leu | Ser | Met | Ser | Tyr | Asn | Leu |
| | | | | Leu | Gly | Phe | Leu | Gln | Arg |
| Ser | Ser | Asn | Phe | Gln | Cys | Gln | Lys | Leu | Leu |
| | | | | Trp | Gln | Leu | Asn | Gly | Arg |
| Leu | Glu | Tyr | Cys | Leu | Lys | Asp | Arg | Met | Asn |
| | | | | Phe | Asp | Ile | Pro | Glu | Glu |
| Ile | Lys | Gln | Leu | Gln | Gln | Phe | Gln | Lys | Glu |
| | | | | Asp | Ala | Ala | Leu | Thr | Ile |
| Tyr | Glu | Met | Leu | Gln | Asn | Ile | Phe | Ala | Ile |
| | | | | Phe | Arg | Gln | Asp | Ser | Ser |
| Ser | Thr | Gly | Trp | Asn | Glu | Thr | Ile | Val | Glu |
| | | | | Asn | Leu | Leu | Ala | Asn | Val |
| Tyr | His | Gln | Ile | Asn | His | Leu | Lys | Thr | Val |
| | | | | Leu | Glu | Glu | Lys | Leu | Glu |
| Lys | Glu | Asp | Phe | Thr | Arg | Gly | Lys | Leu | Met |
| | | | | Ser | Ser | Leu | His | Leu | Lys |
| Arg | Tyr | Tyr | Gly | Arg | Ile | Leu | His | Tyr | Leu |
| | | | | Lys | Ala | Lys | Glu | Tyr | Ser |
| His | Cys | Ala | Trp | Thr | Ile | Val | Arg | Val | Glu |
| | | | | Ile | Leu | Arg | Asn | Phe | Tyr |
| Phe | Ile | Asn | Arg | Leu | Thr | Gly | Tyr | Leu | Arg |
| | | | | | | | | | Asn | in a vector DNA.

16. The process according to claim 15 wherein said vector DNA is an *Escherichia coli* plasmid.

17. A process according to claim 16 wherein said *Escherichia coli* plasmid is selected from the group consisting of pBR322, pCR1 and pMB9.

18. A process for preparing a recombinant plasmid which comprises inserting a synthesized double stranded DNA which codes for the amino acid sequence:

| Met | Ser | Tyr | Asn | Leu | Leu | Gly | Phe | Leu | Gln | Arg | Ser | Ser | Asn | Phe | Gln |
|---|---|---|---|---|---|---|---|---|---|---|---|---|---|---|---|
| Cys | Gln | Lys | Leu | Leu | Trp | Gln | Leu | Asn | Gly | Arg | Leu | Glu | Tyr | Cys | Leu |
| Lys | Asp | Arg | Met | Asn | Phe | Asp | Ile | Pro | Glu | Glu | Ile | Lys | Gln | Leu | Gln |
| Gln | Phe | Gln | Lys | Glu | Asp | Ala | Ala | Leu | Thr | Ile | Tyr | Glu | Met | Leu | Gln |
| Asn | Ile | Phe | Ala | Ile | Phe | Arg | Gln | Asp | Ser | Ser | Ser | Thr | Gly | Trp | Asn |
| Glu | Thr | Ile | Val | Glu | Asn | Leu | Leu | Ala | Asn | Val | Tyr | His | Gln | Ile | Asn |
| His | Leu | Lys | Thr | Val | Leu | Glu | Glu | Lys | Leu | Glu | Lys | Glu | Asp | Phe | Thr |
| Arg | Gly | Lys | Leu | Met | Ser | Ser | Leu | His | Leu | Lys | Arg | Tyr | Tyr | Gly | Arg |
| Ile | Leu | His | Tyr | Leu | Lys | Ala | Lys | Glu | Tyr | Ser | Ais | Cys | Ala | Trp | Thr |
| Ile | Val | Arg | Val | Glu | Ile | Leu | Arg | Asn | Phe | Tyr | Phe | Ile | Asn | Arg | Leu |
| Thr | Gly | Tyr | Leu | Arg | Asn |  |  |  |  |  |  |  |  |  |  | in a vector DNA.

19. The process according to claim 18 wherein said vector DNA is an *Escherichia coli* plasmid.

20. A process according to claim 19 wherein said *Escherichia coli* plasmid is selected from the group consisting of pBR322, pCR1 and pMB9.

21. A process for producing a microorganism capable of expression of a polypeptide with interferon activity which comprises transforming a host microorganism with a replicable recombinant plasmid containing a foreign DNA which codes for the amino acid sequence:

| Met | Thr | Asn | Lys | Cys | Leu | Leu | Gln | Ile | Ala | Leu | Leu | Leu | Cys | Phe | Ser |
|---|---|---|---|---|---|---|---|---|---|---|---|---|---|---|---|
| Thr | Thr | Ala | Leu | Ser | Met | Ser | Tyr | Asn | Leu | Leu | Gly | Phe | Leu | Gln | Arg |
| Ser | Ser | Asn | Phe | Gln | Cys | Gln | Lys | Leu | Leu | Trp | Gln | Leu | Asn | Gly | Arg |
| Leu | Glu | Tyr | Cys | Leu | Lys | Asp | Arg | Met | Asn | Phe | Asp | Ile | Pro | Glu | Glu |
| Ile | Lys | Gln | Leu | Gln | Gln | Phe | Gln | Lys | Glu | Asp | Ala | Ala | Leu | Thr | Ile |
| Tyr | Glu | Met | Leu | Gln | Asn | Ile | Phe | Ala | Ile | Phe | Arg | Gln | Asp | Ser | Ser |
| Ser | Thr | Gly | Trp | Asn | Glu | Thr | Ile | Val | Glu | Asn | Leu | Leu | Ala | Asn | Val |
| Tyr | His | Gln | Ile | Asn | His | Leu | Lys | Thr | Val | Leu | Glu | Glu | Lys | Leu | Glu |
| Lys | Glu | Asp | Phe | Thr | Arg | Gly | Lys | Leu | Met | Ser | Ser | Leu | His | Leu | Lys |
| Arg | Tyr | Tyr | Gly | Arg | Ile | Leu | His | Tyr | Leu | Lys | Ala | Lys | Glu | Tyr | Ser |
| His | Cys | Ala | Trp | Thr | Ile | Val | Arg | Val | Glu | Ile | Leu | Arg | Asn | Phe | Tyr |
| Phe | Ile | Asn | Arg | Leu | Thr | Gly | Tyr | Leu | Arg | Asn. |  |  |  |  |  |

22. A process according to claim 21 wherein said host microorganism is *Escherichia coli* χ1776.

23. A process according to claim 21 wherein said recombinant plasmid is TpIF 319-13.

24. A process for producing a microorganism capable of expression of a polypeptide with interferon activity which comprises transforming a host microorganism with a replicable recombinant plasmid containing a foreign DNA which codes for the amino acid sequence:

| Met | Ser | Tyr | Asn | Leu | Leu | Gly | Phe | Leu | Gln | Arg | Ser | Ser | Asn | Phe | Gln |
|---|---|---|---|---|---|---|---|---|---|---|---|---|---|---|---|
| Cys | Gln | Lys | Leu | Leu | Trp | Gln | Leu | Asn | Gly | Arg | Leu | Glu | Tyr | Cys | Leu |
| Lys | Asp | Arg | Met | Asn | Phe | Asp | Ile | Pro | Glu | Glu | Ile | Lys | Gln | Leu | Gln |
| Gln | Phe | Gln | Lys | Glu | Asp | Ala | Ala | Leu | Thr | Ile | Tyr | Glu | Met | Leu | Gln |
| Asn | Ile | Phe | Ala | Ile | Phe | Arg | Gln | Asp | Ser | Ser | Ser | Thr | Gly | Trp | Asn |
| Glu | Thr | Ile | Val | Glu | Asn | Leu | Leu | Ala | Asn | Val | Tyr | His | Gln | Ile | Asn |
| His | Leu | Lys | Thr | Val | Leu | Glu | Glu | Lys | Leu | Glu | Lys | Glu | Asp | Phe | Thr |
| Arg | Gly | Lys | Leu | Met | Ser | Ser | Leu | His | Leu | Lys | Arg | Tyr | Tyr | Gly | Arg |
| Ile | Leu | His | Tyr | Leu | Lys | Ala | Lys | Glu | Tyr | Ser | His | Cys | Ala | Trp | Thr |
| Ile | Val | Arg | Val | Glu | Ile | Leu | Arg | Asn | Phe | Tyr | Phe | Ile | Asn | Arg | Leu |
| Thr | Gly | Tyr | Leu | Arg | Asn. |  |  |  |  |  |  |  |  |  |  |

25. A process according to claim 24 wherein said host microorganism is *Escherichia coli* χ1776.

26. A recombinant expression plasmid for producing human fibroblast $\beta_1$ interferon, comprising a DNA sequence coding for human fibroblast $\beta_1$ interferon operably linked therein for expression by an *Escherichia coli* host, whereby expression of human fibroblast β₁ interferon by said host is enabled.

27. An *Escherichia coli* host cell capable of expressing human fibroblast β₁ interferon polypeptide, transformed with an expression plasmid of claim 26.

28. An *Escherichia coli* host cell of claim 27, wherein said DNA has the sequence:

| | | | | | | | | | | | | | | |
|---|---|---|---|---|---|---|---|---|---|---|---|---|---|---|
| ATG | ACC | AAC | AAG | TGT | CTC | CTC | CAA | ATT | GCT | CTC | CTG | TTG | TGC | TTC | TCC |
| TAC | TGG | TTG | TTC | ACA | GAG | GAG | GTT | TAA | CGA | GAG | GAC | AAC | ACG | AAG | AGG |
| ACT | ACA | GCT | CTT | TCC | ATG | AGC | TAC | AAC | TTG | CTT | GGA | TTC | CTA | CAA | AGA |
| TGA | TGT | CGA | GAA | AGG | TAC | TCG | ATG | TTG | AAC | GAA | CCT | AAG | GAT | GTT | TCT |
| AGC | AGC | AAT | TTT | CAG | TGT | CAG | AAG | CTC | CTG | TGG | CAA | TTG | AAT | GGG | AGG |
| TCG | TCG | TTA | AAA | GTC | ACA | GTC | TTC | GAG | GAC | ACC | GTT | AAC | TTA | CCC | TCC |
| CTT | GAA | TAT | TGC | CTC | AAG | GAC | AGG | ATG | AAC | TTT | GAC | ATC | CCT | GAG | GAG |
| GAA | CTT | ATA | ACG | GAG | TTC | CTG | TCC | TAC | TTG | AAA | CTG | TAG | GGA | CTC | CTC |
| ATT | AAG | CAG | CTG | CAG | CAG | TTC | CAG | AAG | GAG | GAC | GCC | GCA | TTG | ACC | ATC |
| TAA | TTC | GTC | GAC | GTC | GTC | AAG | GTC | TTC | CTC | CTG | CGG | CGT | AAC | TGG | TAG |
| TAT | GAG | ATG | CTC | CAG | AAC | ATC | TTT | GCT | ATT | TTC | AGA | CAA | GAT | TCA | TCT |
| ATA | CTC | TAC | GAG | GTC | TTG | TAG | AAA | CGA | TAA | AAG | TCT | GTT | CTA | AGT | AGA |
| AGC | ACT | GGC | TGG | AAT | GAG | ACT | ATT | GTT | GAG | AAC | CTC | CTG | GCT | AAT | GTC |
| TCG | TGA | CCG | ACC | TTA | CTC | TGA | TAA | CAA | CTC | TTG | GAG | GAC | CGA | TTA | CAG |
| TAT | CAT | CAG | ATA | AAC | CAT | CTG | AAG | ACA | GTC | CTG | GAA | GAA | AAA | CTG | GAG |
| ATA | GTA | GTC | TAT | TTG | GTA | GAC | TTC | TGT | CAG | GAC | CTT | CTT | TTT | GAC | CTC |
| AAA | GAA | GAT | TTC | ACC | AGG | GGA | AAA | CTC | ATG | AGC | AGT | CTG | CAC | CTG | AAA |
| TTT | CTT | CTA | AAG | TGG | TCC | CCT | TTT | GAG | TAC | TCG | TCA | GAC | GTG | GAC | TTT |
| AGA | TAT | TAT | GGG | AGG | ATT | CTG | CAT | TAC | CTG | AAG | GCC | AAG | GAG | TAC | AGT |
| TCT | ATA | ATA | CCC | TCC | TAA | GAC | GTA | ATG | GAC | TTC | CGG | TTC | CTC | ATG | TCA |
| CAC | TGT | GCC | TGG | ACC | ATA | GTC | AGA | GTG | GAA | ATC | CTA | AGG | AAC | TTT | TAC |
| GTG | ACA | CGG | ACC | TGG | TAT | CAG | TCT | CAC | CTT | TAG | GAT | TCC | TTG | AAA | ATG |
| TTC | ATT | AAC | AGA | CTT | ACA | GGT | TAC | CTC | CGA | AAC | | | | | |
| AAG | TAA | TTG | TCT | GAA | TGT | CCA | ATG | GAG | GCT | TTG. | | | | | |

29. A method of producing human fibroblast β₁ interferon polypeptide, comprising expressing the expression plasmid of claim 26 in *Escherichia coli*.

30. A method of claim 29, wherein said DNA has the sequence:

| | | | | | | | | | | | | | | |
|---|---|---|---|---|---|---|---|---|---|---|---|---|---|---|
| ATG | ACC | AAC | AAG | TGT | CTC | CTC | CAA | ATT | GCT | CTC | CTG | TTG | TGC | TTC | TCC |
| TAC | TGG | TTG | TTC | ACA | GAG | GAG | GTT | TAA | CGA | GAG | GAC | AAC | ACG | AAG | AGG |
| ACT | ACA | GCT | CTT | TCC | ATG | AGC | TAC | AAC | TTG | CTT | GGA | TTC | CTA | CAA | AGA |
| TGA | TGT | CGA | GAA | AGG | TAC | TCG | ATG | TTG | AAC | GAA | CCT | AAG | GAT | GTT | TCT |
| AGC | AGC | AAT | TTT | CAG | TGT | CAG | AAG | CTC | CTG | TGG | CAA | TTG | AAT | GGG | AGG |
| TCG | TCG | TTA | AAA | GTC | ACA | GTC | TTC | GAG | GAC | ACC | GTT | AAC | TTA | CCC | TCC |
| CTT | GAA | TAT | TGC | CTC | AAG | GAC | AGG | ATG | AAC | TTT | GAC | ATC | CCT | GAG | GAG |
| GAA | CTT | ATA | ACG | GAG | TTC | CTG | TCC | TAC | TTG | AAA | CTG | TAG | GGA | CTC | CTC |
| ATT | AAG | CAG | CTG | CAG | CAG | TTC | CAG | AAG | GAG | GAC | GCC | GCA | TTG | ACC | ATC |
| TAA | TTC | GTC | GAC | GTC | GTC | AAG | GTC | TTC | CTC | CTG | CGG | CGT | AAC | TGG | TAG |
| TAT | GAG | ATG | CTC | CAG | AAC | ATC | TTT | GCT | ATT | TTC | AGA | CAA | GAT | TCA | TCT |
| ATA | CTC | TAC | GAG | GTC | TTG | TAG | AAA | CGA | TAA | AAG | TCT | GTT | CTA | AGT | AGA |
| AGC | ACT | GGC | TGG | AAT | GAG | ACT | ATT | GTT | GAG | AAC | CTC | CTG | GCT | AAT | GTC |
| TCG | TGA | CCG | ACC | TTA | CTC | TGA | TAA | CAA | CTC | TTG | GAG | GAC | CGA | TTA | CAG |
| TAT | CAT | CAG | ATA | AAC | CAT | CTG | AAG | ACA | GTC | CTG | GAA | GAA | AAA | CTG | GAG |
| ATA | GTA | GTC | TAT | TTG | GTA | GAC | TTC | TGT | CAG | GAC | CTT | CTT | TTT | GAC | CTC |
| AAA | GAA | GAT | TTC | ACC | AGG | GGA | AAA | CTC | ATG | AGC | AGT | CTG | CAC | CTG | AAA |
| TTT | CTT | CTA | AAG | TGG | TCC | CCT | TTT | GAG | TAC | TCG | TCA | GAC | GTG | GAC | TTT |
| AGA | TAT | TAT | GGG | AGG | ATT | CTG | CAT | TAC | CTG | AAG | GCC | AAG | GAG | TAC | AGT |
| TCT | ATA | ATA | CCC | TCC | TAA | GAC | GTA | ATG | GAC | TTC | CGG | TTC | CTC | ATG | TCA |
| CAC | TGT | GCC | TGG | ACC | ATA | GTC | AGA | GTG | GAA | ATC | CTA | AGG | AAC | TTT | TAC |
| GTG | ACA | CGG | ACC | TGG | TAT | CAG | TCT | CAC | CTT | TAG | GAT | TCC | TTG | AAA | ATG |
| TTC | ATT | AAC | AGA | CTT | ACA | GGT | TAC | CTC | CGA | AAC | | | | | |
| AAG | TAA | TTG | TCT | GAA | TGT | CCA | ATG | GAG | GCT | TTG. | | | | | |

31. A plasmid of claim 26, wherein said DNA has the sequence:

| ATG | ACC | AAC | AAG | TGT | CTC | CTC | CAA | ATT | GCT | CTC | CTG | TTG | TGC | TTC | TCC |
|-----|-----|-----|-----|-----|-----|-----|-----|-----|-----|-----|-----|-----|-----|-----|-----|
| TAC | TGG | TTG | TTC | ACA | GAG | GAG | GTT | TAA | CGA | GAG | GAC | AAC | ACG | AAG | AGG |
| ACT | ACA | GCT | CTT | TCC | ATG | AGC | TAC | AAC | TTG | CTT | GGA | TTC | CTA | CAA | AGA |
| TGA | TGT | CGA | GAA | AGG | TAC | TCG | ATG | TTG | AAC | GAA | CCT | AAG | GAT | GTT | TCT |
| AGC | AGC | AAT | TTT | CAG | TGT | CAG | AAG | CTC | CTG | TGG | CAA | TTG | AAT | GGG | AGG |
| TCG | TCG | TTA | AAA | GTC | ACA | GTC | TTC | GAG | GAC | ACC | GTT | AAC | TTA | CCC | TCC |
| CTT | GAA | TAT | TGC | CTC | AAG | GAC | AGG | ATG | AAC | TTT | GAC | ATC | CCT | GAG | GAG |
| GAA | CTT | ATA | ACG | GAG | TTC | CTG | TCC | TAC | TTG | AAA | CTG | TAG | GGA | CTC | CTC |
| ATT | AAG | CAG | CTG | CAG | CAG | TTC | CAG | AAG | GAG | GAC | GCC | GCA | TTG | ACC | ATC |
| TAA | TTC | GTC | GAC | GTC | GTC | AAG | GTC | TTC | CTC | CTG | CGG | CGT | AAC | TGG | TAG |
| TAT | GAG | ATG | CTC | CAG | AAC | ATC | TTT | GCT | ATT | TTC | AGA | CAA | GAT | TCA | TCT |
| ATA | CTC | TAC | GAG | GTC | TTG | TAG | AAA | CGA | TAA | AAG | TCT | GTT | CTA | AGT | AGA |
| AGC | ACT | GGC | TGG | AAT | GAG | ACT | ATT | GTT | GAG | AAC | CTC | CTG | GCT | AAT | GTC |
| TCG | TGA | CCG | ACC | TTA | CTC | TGA | TAA | CAA | CTC | TTG | GAG | GAC | CGA | TTA | CAG |
| TAT | CAT | CAG | ATA | AAC | CAT | CTG | AAG | ACA | GTC | CTG | GAA | GAA | AAA | CTG | GAG |
| ATA | GTA | GTC | TAT | TTG | GTA | GAC | TTC | TGT | CAG | GAC | CTT | CTT | TTT | GAC | CTC |
| AAA | GAA | GAT | TTC | ACC | AGG | GGA | AAA | CTC | ATG | AGC | AGT | CTG | CAC | CTG | AAA |
| TTT | CTT | CTA | AAG | TGG | TCC | CCT | TTT | GAG | TAC | TCG | TCA | GAC | GTG | GAC | TTT |
| AGA | TAT | TAT | GGG | AGG | ATT | CTG | CAT | TAC | CTG | AAG | GCC | AAG | GAG | TAC | AGT |
| TCT | ATA | ATA | CCC | TCC | TAA | GAC | GTA | ATG | GAC | TTC | CGG | TTC | CTC | ATG | TCA |
| CAC | TGT | GCC | TGG | ACC | ATA | GTC | AGA | GTG | GAA | ATC | CTA | AGG | AAC | TTT | TAC |
| GTG | ACA | CGG | ACC | TGG | TAT | CAG | TCT | CAC | CTT | TAG | GAT | TCC | TTG | AAA | ATG |
| TTC | ATT | AAC | AGA | CTT | ACA | GGT | TAC | CTC | CGA | AAC | | | | | |
| AAG | TAA | TTG | TCT | GAA | TGT | CCA | ATG | GAG | GCT | TTG. | | | | | |

* * * * *